(12) United States Patent
Pfaller

(10) Patent No.: US 6,329,195 B1
(45) Date of Patent: Dec. 11, 2001

(54) CELL CULTURE APPARATUS

(75) Inventor: Walter Pfaller, Innsbruch (AT)

(73) Assignee: ACM-Biotech GmbH, Munich (DE)

( * ) Notice: Subject to any disclaimer, the term of this patent is extended or adjusted under 35 U.S.C. 154(b) by 0 days.

(21) Appl. No.: 09/451,969

(22) Filed: Nov. 30, 1999

(51) Int. Cl.[7] .................................................. C12M 3/06
(52) U.S. Cl. ...................... 435/297.2; 435/287.1; 435/297.5
(58) Field of Search .................... 435/287.1, 287.9, 435/297.1, 297.2, 297.5

(56) References Cited

U.S. PATENT DOCUMENTS

| 4,225,671 | * | 9/1980 | Puchinger et al. . | |
| 4,608,342 | | 8/1986 | Nees | 435/240 |
| 4,748,124 | * | 5/1988 | Vogler . | |
| 4,762,794 | * | 8/1988 | Nees . | |
| 4,835,102 | * | 5/1989 | Bell et al. . | |
| 5,190,878 | | 3/1993 | Wilhelm | 435/285 |
| 5,409,829 | | 4/1995 | Mussi et al. | 435/240.2 |
| 5,459,068 | * | 10/1995 | Madara . | |
| 5,658,797 | * | 8/1997 | Bader . | |
| 5,688,687 | | 11/1997 | Palsson et al. | 435/293.2 |
| 5,707,869 | | 1/1998 | Wolf et al. | 435/401 |
| 5,714,384 | | 2/1998 | Wilson et al. | 435/401 |
| 5,888,807 | * | 3/1999 | Palsson et al. . | |
| 5,981,268 | | 11/1999 | Kovacs et al. | 435/287 |

FOREIGN PATENT DOCUMENTS

| 727629 | 11/1998 | (AT) . |
| 3246092 | 6/1984 | (DE) . |
| 3923279 | 7/1989 | (DE) . |
| 19719751 | 11/1998 | (DE) . |
| 0307048 | 3/1989 | (EP) . |
| 0890636 | 1/1999 | (EP) . |

* cited by examiner

Primary Examiner—William H. Beisner
(74) Attorney, Agent, or Firm—Hamilton, Brook, Smith & Reynolds

(57) ABSTRACT

A cell culture apparatus includes at least one growth support for cells which borders on at least one side to a culture medium compartment which is suppliable, preferably continuously, with liquid culture media via inflow and outflow openings. The cell culture apparatus includes at least one gas compartment which is suppliable with a defined gas or mixture of gases, wherein said gas compartment borders to the culture medium compartment via a gas permeable but liquid impermeable membrane.

19 Claims, 3 Drawing Sheets

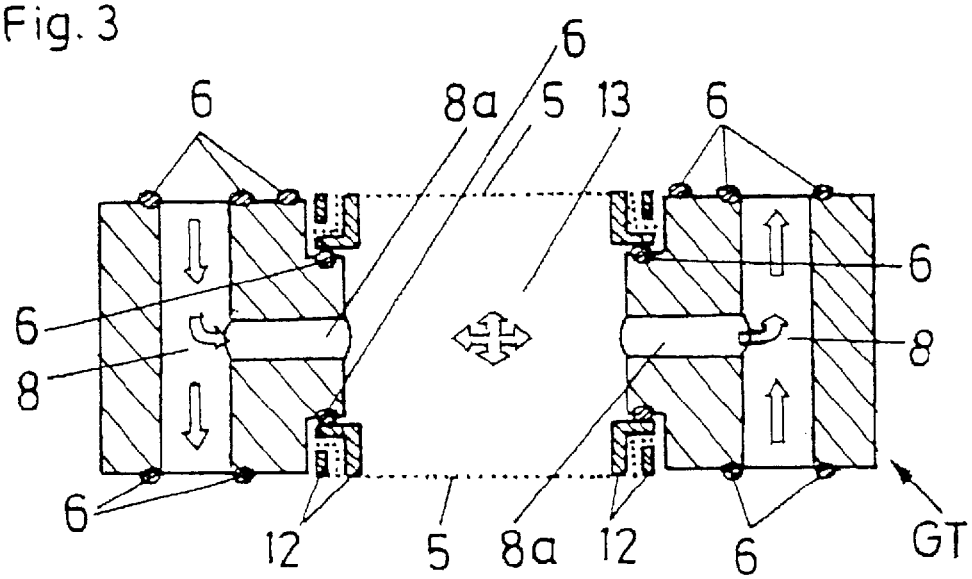
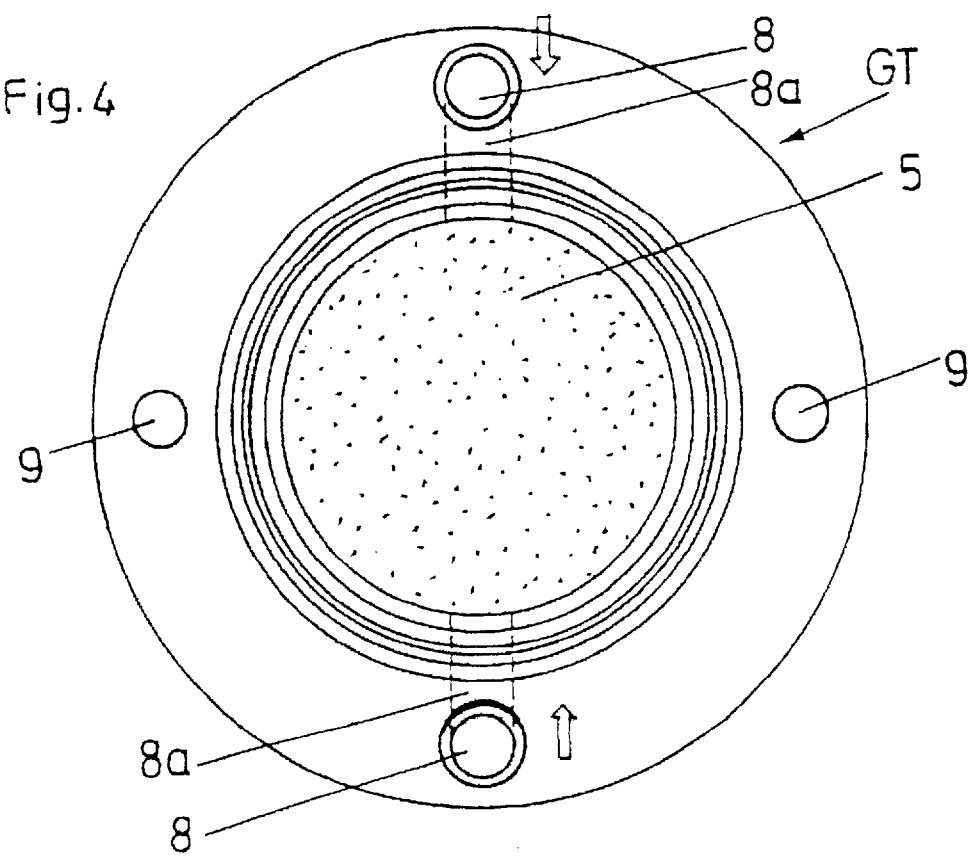

CELL CULTURE APPARATUS

BACKGROUND OF THE INVENTION

Cells can be taken from tissues and grown or proliferated extracorporally. Under these conditions, some cell types develop properties which allow unlimited propagation, through permanently repeated mitoses. These cells are denoted as so-called permanent cell lines. Freshly removed cells from tissues (e.g., surgical samples, or tissues from experimental animals) most often do not display these properties. Cells of such so-called primary cultures either lack mitotic activity or perform only a few mitoses, i.e., these cells can only be cultured for a short period of time and only under loss of most of their original functional characteristics (dedifferentiation).

Adhesion of cells to their growth support and the appropriate differentiation of cells is largely dependent on the properties of the growth support (growth substrate).

The introduction of microporous growth supports made up of thin foils of either organic or inorganic materials led to an improvement in differentiation of cells in culture. This is specifically the case for those cells growing as monocellular layers (monolayers) like epithelial and endothelial cells. The culture containers used for that purpose in most cases are hollow cylinders which are sealed on one side by microporous foils on which cells are growing. These cylinders are then placed into larger culture containers in a way that culture medium can reach the cell monolayers from both the apical and the basolateral side (U.S. Pat. No. 4,608,342), the teachings of which are incorporated herein by reference. The culture medium is replaced at certain intervals. Cultures of this type are denoted as "static". Under these conditions, compounds produced by cells can accumulate in the culture medium and exert negative effects on cell growth and differentiation. For this reason, improved conditions have been developed. Microporous growth substrates can, for example, be placed between two concentric circular mounting unites (cell carrier) and then cells seeded and attached to the growth support. Such cell carriers can then be transferred to a culture medium chamber which is separated by the carrier in two halves. Each half of the chamber can then be perfused with the same medium or media differing in composition. The cell carriers can also be stapled in a specific culture chamber and per(i)fused with culture medium (DE-PS 3923 279), the teachings of which are incorporated herein by reference. These cell culture systems are easy to handle and offer the possibility to grow and/or maintain primary cultures over longer periods of time than under static culture conditions either using solid (plastic, glass) or microporous supports. However, they have the disadvantage that only culture containers for cell carriers having a very small growth area, i.e., about 0.9 cm$^2$, are obtainable. The per(i)fusion cell apparatus in which cell carriers can be stacked in order to obtain enough material for biochemical/cell biological analyses has the disadvantage of insufficient oxygenation of the medium between the cell carriers. Furthermore, both devices display mixing inhomogenities during continuous replacement of the growth medium by per(i)fusion.

SUMMARY OF THE INVENTION

The invention relates to a cell culture apparatus or cell culture device, respectively, with at least one growth support for cells, which borders at least on one side to a culture medium space preferably supplied with liquid medium in a continuous mode via inflow and outflow openings.

The present invention relates to a cell culture apparatus which allows the growth and maintenance of cell cultures over prolonged periods of time under conditions which closely resemble the situation within the intact organisms. According to the invention, this can be achieved by implementation of at least one gas-compartment which can be filled with a single gas or a mixture of gases and which is sealed towards the culture medium container by a membrane impermeable to liquids but permeable to gases. This allows that within the culture medium, which is in immediate contact with the cultured cells defined partial pressures (p) of oxygen ($O_2$), carbon dioxide ($CO_2$), nitrogen ($N_2$), or other gases of biological or toxicological significance can be maintained. This is of specific importance, because the cell culture systems utilizing continuous replacement of culture medium available so far do not offer this possibility. None of the systems available ensures the maintenance of constant partial pressures for biologically relevant gases like oxygen or carbon dioxide. Additional advantages and details of the invention are listed below and are further illustrated by the respective figures.

BRIEF DESCRIPTION OF THE DRAWINGS

FIG. 3 shows in a vertical central section the gas part of the cell culture apparatus according to the invention.

FIG. 4 gives the respective upside down view, and

DETAILED DESCRIPTION OF THE INVENTION

Figure 1:
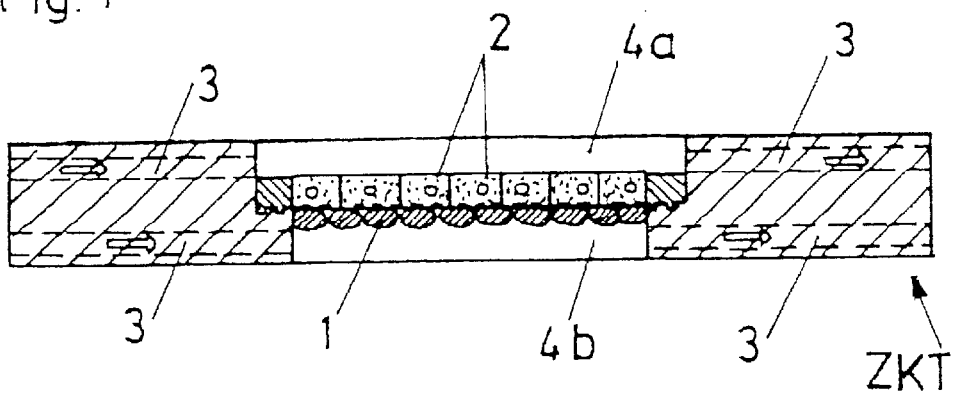
FIG. 1 gives in a vertical section an example of a cell culture part of the cell culture apparatus according to the invention.
Figure 2:
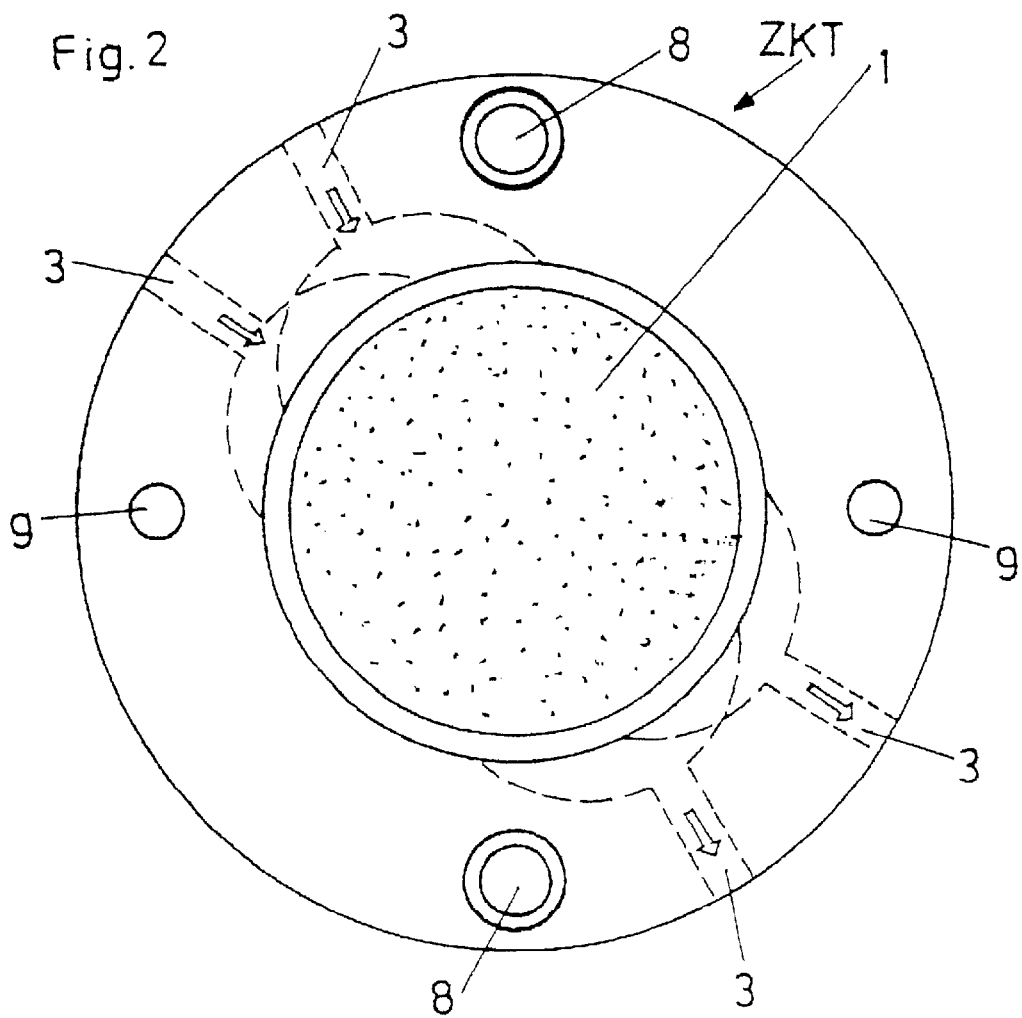
FIG. 2 gives the respective upside down view.
Figure 5:
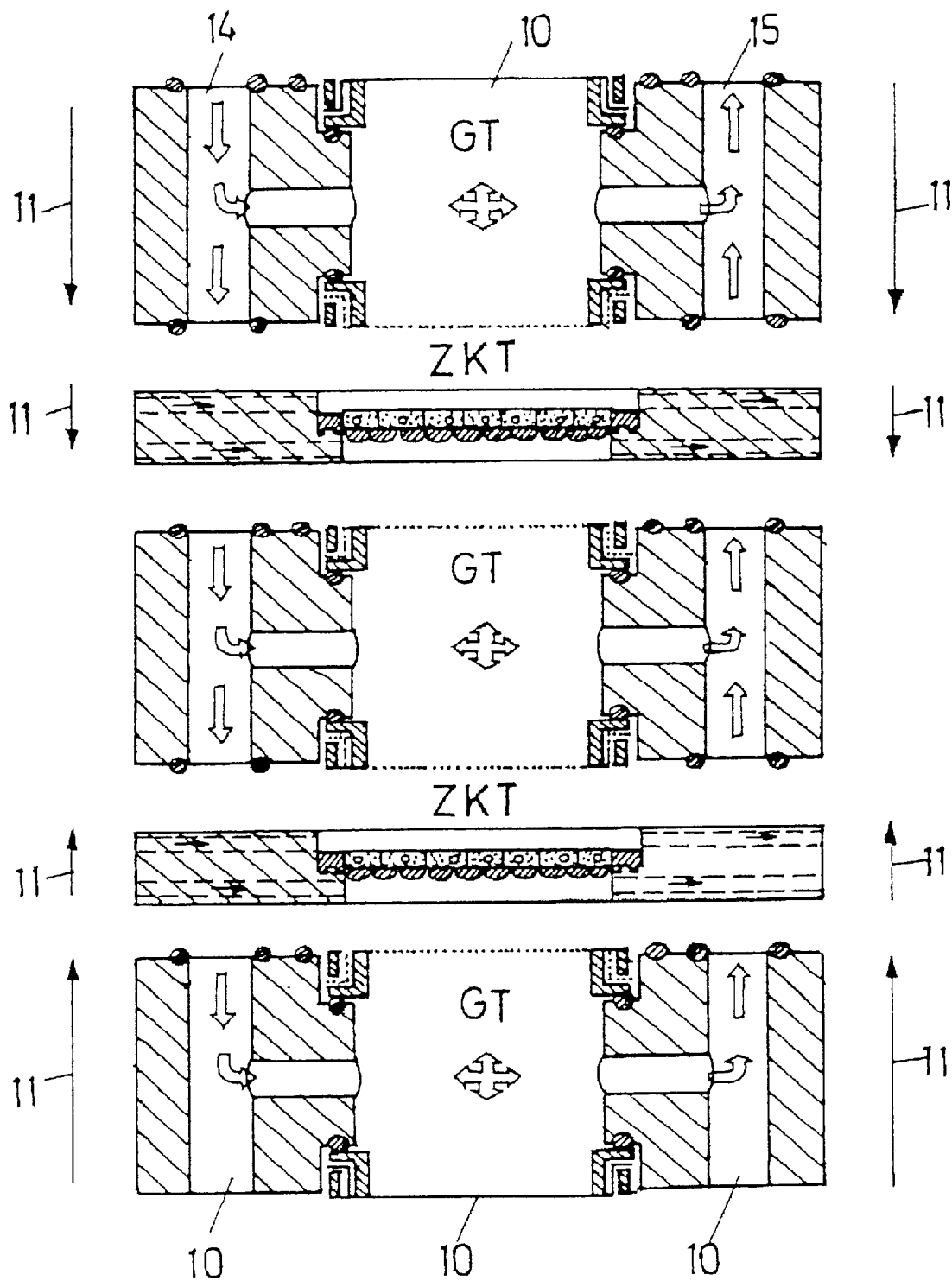
FIG. 5 shows in a schematic vertical section of an assembly consisting of two cell culture parts and three gas parts of the cell culture apparatus according to the invention.

The cell culture apparatus model according to the invention includes a cell culture part (FIGS. 1 and 2) and a gas part (FIGS. 3 and 4) which for example can be assembled as shown in FIG. 5.

The cell culture part (ZKT) represents a ring-shaped mounting piece for a microporous growth support 1, which ensures optimum exchange of nutrients between cell culture medium and cells 2 (in this case two monolayers) thereby improving the special differentiation of cells. The administration and removal of culture media into the upper 4a and the lower 4b culture medium compartment of the cell culture part, ZKT, is performed via separate channels 3 for each side of the growth support. The cell culture apparatus or cell culture device, respectively, with at least one growth support for cells, which can be proximate or contiguous with culture medium space or compartment, is preferably supplied with liquid medium in a continuous mode via inflow and outflow openings. Inflow and outflow channels are designed to provide homogeneous replacement of medium and to prevent uneven mixture of medium. This design further offers the possibility to perfuse nutrients of different composition at the top (apical) and bottom (basal or basolateral, respectively) side of the growth support of the cell culture part, thereby providing organotypic culture conditions.

The cell culture part, ZKT, is separated from the gas part, GT, through a membrane 5, preferentially made of polytetrafluoroethylene, impermeable for liquid nutrients but freely permeable for gases. The gas part is designed as a separate unit of the cell culture apparatus and has the same cylindrical outer measures as the cell culture part of FIGS. 1 and 2. The gas part shown in FIG. 3 is equipped with a gas permeable membrane 5 at both sides, and is fixed with a special mounting unit 12 to achieve a gas tight seal. The gas region or gas space or gas compartment 13 is located between the two membranes 5 and connected via vertical channels 8 to a gas supply reservoir (not shown) via tubing (not shown) which allow the supply of gas in the desired concentration. The gas flows also via the vertical channels contained in the cell culture parts aligned to the top and the bottom of the gas part.

The growth support 1 for the cells to be cultured 2 are easily exchangeable so that biochemical and molecular biological parameters can easily by analyzed. The gas permeable membrane 5 can also easily be replaced. The gas part, GT (including the vertical gas channel 8), and the mounting unit 12 for the gas permeable membrane 5 are sealed against the cell culture part, ZKT, by o-rings 6. Gas parts, GT, and cell culture parts, ZKT, can be stapled as shown in FIG. 5. This allows the simultaneous cultivation of many (as many as desired) cell growth supports under conditions of continuous nutrient supply. The assembly is performed in the direction of the arrows 11. The screw-mount through aligned bores 9 (screws not shown) presses and seals all parts together. The growth area of a single growth support amounts to approximately 5 cm$^2$.

All gas parts are connected via a channel 8 so that only one gas input connection and one gas output connection is preferred. From the channel 8 side, channels 8a are branching off to the gas space of the gas part. The sealing between the gas channels, the gas part and the cell culture part again is performed by o-rings 6.

The two ends of the cell culture apparatus are closed with gas parts which have only one gas-permeable membrane on that side which is facing the cell culture part. The remainder is sealed tightly at position 10.

Since the distance between the membrane 5 of the gas region and the growth support of the cell culture part is small, the volume of the apical and basolateral liquid compartment (4a and 4b) is also small. Therefore, a quick equilibration between the gas phase in the gas part, GT, and the gases dissolved in the medium compartments of the cell culture part, ZKT, can be achieved and kept constant.

The foregoing and other objects, features and advantages of the invention will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

The cell culture apparatus according to the invention allows an easy change of gas partial pressures in the culture medium as well as a simple admixture of gases which may influence the function of cultivated cells (gaseous anaesthetics, nitrogen-monoxide). The partial pressures of the gases used can be measured within the gas part, GT, as well as within the cell culture part, ZKT, if necessary, using commercially available electrodes ($O_2$, Clark-electrodes, $CO_2$ or NO electrodes). For that purpose, appropriate o-ring sealed bores (not shown) are foreseen.

In a preferential type of the cell culture part, specifically for the cultivation of epithelial and endothelial cells or the co-cultivation of both cell types on the same growth support, electrodes for the injection of electrical current and electrodes for the continuous monitoring of potential differences brought about by the vectorial transport of charged solutes (ions) can be implemented. Current injections and registration of trans-monolayer potential differences can be performed with commercially available instrumentation. From the injected current and the resulting change in potential differences, the trans-monolayer resistance and the trans-monolayer electrical conductivity can be calculated (principle of an "Ussing" chamber). Cell culture part, ZKT, and gas part, GT, are for example made from Polysulfon and can be autoclaved according to procedures as normally provided by medical authorities. All parts of the cell culture apparatus can be used repetitively although all parts can also be manufactured as one-way articles. The o-rings used for sealing should be made from either Viton or silicone-rubber. Commercially available filter membranes can be used as microporous growth supports.

The invention is not restricted to the modes of application shown. Specifically, the form of the culture medium compartments, ZKT, and of the gas compartments, GT, as well as the respective cell culture and gas parts, can deviate from the geometry shown. In principle, the invention can also be used if only one side of the growth support covered with cells is supplied with nutrient media. The connection between cell culture part, ZKT, and gas part, GT, can be performed by any other connection material than screws, e.g., clips or similar mounting systems.

Possible applications of the cell culture apparatus according to the present invention (hereinafter referred to as Pfaller's chamber, denoted as PK) include: cultures of human, animal, plant and insect cells, as well as organs or parts thereof, derived from any species, under static as well as dynamic culturing conditions (continuous and pulsed-flow of culture media, gases and body fluids); co-cultures of different cells and/or organs or parts thereof under static as well as dynamic culturing conditions (continuous and pulsed-flow of culture media, gases and body fluids); co-cultures of different cells and/or organs or parts thereof under status as well as dynamic culturing conditions (continuous and pulsed-flow of culture media, gases and body fluids) with cell-cell contact; and co-cultures of different cells and/or organs or parts thereof under static as well as dynamic culturing conditions (continuous and pulsed-flow of culture media, gases and body fluids) without reciprocal cell contact (culturing in separated chambers, cell interactions via conditioned medium).

Further possible applications of the cell culture apparatus according to the present invention comprise the development of artificial organs and/or equivalents thereof, by use of the above-mentioned cells and/or organs or parts thereof: cultures and/or co-cultures of astrocytes, glia cells, Schwans's cells and nerve cells, in single or co-culture for investigations of the blood-brain barrier, of conduction of stimulus and of growth studies; cultures and/or co-cultures of corneal epithelial cells together with muscle cells and/or fibroblasts, melanocytes, Langerhans' cells and endothelial cells and microvascular endothelial cells as well as nerve cells; cultures and/or co-cultures of endothelial cells together with muscle cells and/or keratinocytes, fibroblasts, melanocytes, Langerhans' cells and endothelial cells and microvascular endothelial cells as well as nerve cells; cultures and/or co-cultures of keratinocytes, fibroblasts, melanocytes, Langerhans' cells, dendritic cells, endothelial cells and microvascular endothelial cells as well as nerve cells; cultures and/or co-cultures of lung epithelial cells together with keratinocytes, fibroblasts, melanocytes, dendritic cells, endothelial cells and microvascular endothelial cells as well as nerve cells; cultures and/or co-cultures of gastrointestinal epithelial cells together with lymphatic and/or muscle cells, dendritic cells, endothelial cells and microvasular endothelial cells as well as nerve cells; cultures and/or co-cultures of hepatocytes together with fibroblasts, melanocytes, dendritic cells, endothelial cells and microvascular endothelial cells, nerve cells as well as other cells present in the liver (e.g., Kupfer's star cells, etc.); cultures and/or co-cultures of kidney epithelial cells of vascular and/or tubular origin together with lymphatic and/or muscle cells, fibroblasts, dendritic cells, endothelial and microvascular endothelial cells as well as nerve cells; and cultures and/or co-cultures of lymphatic epithelial cells together with lymphatic and/or muscle cells, fibroblasts, melanocytes, dendritic cells, endothelial and microvascular endothelial cells, as well as nerve cells.

Additional applications of the cell culture apparatus according to the present invention include its application with artificial organs and/or equivalents thereof by the use of the above-mentioned cells and/or organs or parts thereof, and/or the application of the artificial organs and/or equivalents thereof which have been generated with the PK by the use of the above cells and/or organs or parts thereof, respectively: models of blood-brain barrier; neuronal models (potentials and conduction of stimuli); drug delivery; examinations of toxicity; effect of light, UV-light, microwave radiation and radiation of higher frequency; studies of cell migration; artificial organs; gas exchange; and implants.

While this invention has been particularly shown and described with references to preferred embodiments thereof, it will be understood by those skilled in the art that various changes in form and details may be made therein without departing from the scope of the invention encompassed by the appended claims.

What is claimed is:

1. A cell culture apparatus comprising at least one cell culture part having a growth support for cells which borders with two culture medium compartments which are suppliable via inflow and outflow openings by liquid culture media; and a gas part having at least one gas space which can be supplied with a gas, wherein said gas space borders the culture medium compartments via a gas permeable, liquid impermeable membrane.

2. The cell culture apparatus of claim 1 wherein said apparatus can operate in a continuous or pulse-flow mode.

3. The cell culture apparatus of claim 1 wherein said gas can include a single gas or a mixture of gases.

4. The cell culture apparatus of claim 1 wherein at least one cell culture part and at least one separate and removable gas part connected thereto, wherein said cell culture part contains at least one growth support for cells and at least one compartment for culture medium, and wherein said gas part includes said gas space and said gas permeable membrane is connected to said cell culture part.

5. The cell culture apparatus of claim 4, where a single cell culture part includes two culture medium compartments.

6. The cell culture apparatus of claim 4, wherein o-ring seals are positioned between cell culture parts and gas parts.

7. The cell culture apparatus; of claim 1 wherein said culture medium compartments are selected from a group comprising an apical compartment, a basal medium compartment, and basolateral medium compartment.

8. The cell culture apparatus of claim 1 wherein said apparatus includes cell culture parts and gas parts which can be assembled in alternating sequence to a staple, whereby the interface gas parts contain two gas permeable membranes, each bordering to the adjacent cell culture part and to gas parts, with one gas permeable membrane and one impermeable closing side.

9. The cell culture apparatus of claim 8, wherein said cell culture parts include drillings parallel to the long axis of a cylinder which allow the insertion of screws to compress the cell culture and gas parts in a tight manner or mode.

10. The cell culture apparatus of claim 9, wherein said drillings include hollow cylinders.

11. The cell culture apparatus of claim 10, wherein said hollow cylinders have the same diameter.

12. The cell culture apparatus of claim 1, wherein said liquid impermeable, gas permeable membrane includes polytetrafluoroethylene.

13. The cell culture apparatus of claim 1, wherein said cell culture part and gas parts are formed of polysulfon.

14. The cell culture apparatus of claim 1 wherein said gas space can be supplied via a removable gas line.

15. The cell culture apparatus of claim 14 wherein said removable gas line is connected to at least one gas reservoir.

16. The cell culture apparatus of claim 1, wherein said apparatus includes a system for measuring partial pressures of the gases used within the cell culture medium compartments.

17. The cell culture apparatus of claim 16, wherein said system for measuring includes an electrode.

18. A cell culture apparatus comprising:
   a) growth support for cells;
   b) two culture medium compartments, which are proximate to said growth support for cells, wherein said compartments include an inflow opening and an outflow opening for liquid culture media; and
   c) a gas compartment, which is proximate to each said culture medium compartment, wherein said gas compartment includes a gas permeable, liquid impermeable membrane which allows passage of gas from said gas compartment to said culture medium compartments.

19. The cell culture apparatus of claim 18, wherein the apparatus includes a growth support with at least one monolayer of cells with implemented electrodes to inject electrical current and electrodes for allowing continuous measurement of potential differences across the monolayer grown on the growth support.

* * * * *